United States Patent [19]

Treybig

[11] Patent Number: 4,837,324
[45] Date of Patent: Jun. 6, 1989

[54] PROCESS FOR THE REACTION OF PIPERAZINE, AND DERIVATIVES THEREOF, WITH GLYOXAL, AND DERIVATIVES THEREOF

[75] Inventor: Duane S. Treybig, Lake Jackson, Tex.

[73] Assignee: The Dow Chemical Company, Midland, Mich.

[21] Appl. No.: 70,981

[22] Filed: Jul. 8, 1987

Related U.S. Application Data

[62] Division of Ser. No. 749,697, Jun. 28, 1985, Pat. No. 4,761,476.

[51] Int. Cl.$^4$ ................. C07D 295/08; C07D 295/10
[52] U.S. Cl. ..................................... 544/357; 544/386
[58] Field of Search ................. 544/357, 386; 548/318

[56] References Cited

U.S. PATENT DOCUMENTS

| | | | |
|---|---|---|---|
| 2,969,365 | 1/1961 | Levis | 544/358 |
| 2,993,900 | 7/1961 | Biel | 544/379 |
| 2,995,554 | 8/1961 | Biel | 544/379 |
| 3,210,396 | 10/1965 | Horvitz | 548/29 |
| 3,280,108 | 10/1966 | Sander et al. | 548/962 |
| 4,094,687 | 6/1978 | Lawton | 544/357 |

FOREIGN PATENT DOCUMENTS 1095866 12/1967 United Kingdom ................ 548/318

OTHER PUBLICATIONS

Kliegman et al., Journal of Heterocyclic Chem., vol. 7, 1970, pp. 1153–1155, "Glyoxal Derivatives, III, The Reaction of Glyoxal with Some Secondary Amines".
Badische Anilin, J. Soda-Fabrik A.G., CA63-18030.g, "Bisaziridines".
Horvitz, CA 63-18030h, "Ethylenehydrazime".
Tajima, CA 89-109493b, (1978), "Cycle Urea-Glyoxal Reaction Products".
Dinwoodie et al., CA 69-10438n, (1968), "2-Imidazolidinone derivatives".
Dinwoodie et al, CA 68-12903p (1968), "Base-Catalyzed Reactions of Glyoxal III, 1,2-Bis(2-Oxo-Imidazolidin-1414 yl) Ethane-1,2-diols".

Primary Examiner—Anton H. Sutto
Assistant Examiner—Cecilia Shen

[57] ABSTRACT

A process for reacting piperazine or alkyl, aryl or aralkyl substituted piperazine with glyoxal or alkyl substituted glyoxal, so as to form corresponding ethanone and ethanediol products is disclosed.

11 Claims, No Drawings

PROCESS FOR THE REACTION OF PIPERAZINE, AND DERIVATIVES THEREOF, WITH GLYOXAL, AND DERIVATIVES THEREOF

RELATED APPLICATIONS

This application is a division of U.S. Ser. No. 749,697, filed 6/28/85 now U.P. Pat. No. 4761476, issued Aug. 2, 1988.

BACKGROUND OF THE INVENTION

1. Field of the Invention

This invention relates to a process for reaction of piperazine or alkyl, aryl or aralkyl substituted piperazine with glyoxal or alkyl substituted glyoxal.

2. Description of the Prior Art

In the article titled "Glyoxal Derivatives. III. The Reaction of Glyoxal with some secondary Amines" by J. M. Kliegman and R. K. Barnes in *Journal of Heterocyclic Chemistry*, Vol. 7, October 1970, pp 1153–1155, the reaction of morpholine, piperidine, N-methylaniline or other secondary amines, and glyoxal is disclosed. The reaction of piperazine and glyoxal is not suggested.

The reaction of a vicinal glycol and piperazine according to U.S. Pat. No. 2,969,365 forms an addition compound. Use of glyoxal as a reactant is not mentioned.

U.S. Pats. Nos. 4,094,687; 2,995,544; and 2,993,900 each relate to reaction products of piperazine. However, use of glyoxal as a reactant is nowhere mentioned.

SUMMARY OF THE INVENTION

The present invention is directed to the reaction process of piperazine or an alkyl, aryl or aralkyl substituted piperazine with glyoxal or alkyl substituted glyoxal.

DETAILED DESCRIPTION

The process of the present invention involves the reaction of a piperazine having the following general formula:

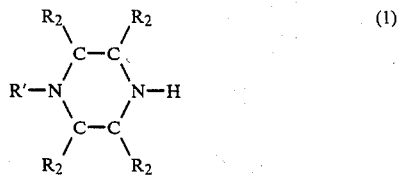

where
 R is hydrogen; $C_1$ to $C_{10}$ alkyl, preferably $C_1$ to $C_4$ alkyl; aryl or aralkyl; and
 R' is hydrogen; $C_1$ to $C_{20}$ alkyl or alkyl with hydroxy substitutents; aryl or aralkyl
with glyoxal (ethanediol) or alkyl substituted glyoxal having the following formula:

where R" is hydrogen or $C_1$ to $C_4$ alkyl.

The preferred reactants are piperazine and glyoxal, however the piperazines substituted by alkyl, aryl or aralkyl groups at the 1,2,3,5 and 6 positions are reactants for forming the compositions of the present invention. Such piperazines are 1-methylpiperazine; 2-methylpiperazine; 2,3- dimethylpiperazine; 2,5-dimethylpiperazine; 2,6-dimethylpiperazine; 1,2-dimethylpiperazine; 1,4-dimethylpiperazine; 1-ethylpiperazine; 2-ethylpiperazine; 2,3-diethylpiperazine; 2,5-diethylpiperazine; 2,6-diethylpiperazine; 1-propylpiperazine; 2-propylpiperazine; 1-ethyl-3-methylpiperazine; 1-butylpiperazine; 2-butylpiperazine; 1-dodecyl1-piperazine; 1-octadecyl-1-piperazine; 1-puperazine ethanol [1-(2-hydroxyethyl)piperazine]; 1-piperazine propanol; 3-piperazino-1,2-propanediol; 1-phenylpiperazine; 2-phenylpiperazine; 2-ethyl-1-phenylpiperazine; 2,3,5,6-tetraphenylpiperazine; mixtures thereof and the like.

Glyoxal dihydrate, 40% aqueous solution of glyoxal, glyoxal hydrogen sulfite and 2,3-dihydroxy-1,4-dioxane are glyoxal equivalents. Glyoxal is liberated from glyoxal hydrogen sulfite with a base. Reactions with 2,3-dihydroxy-1,4-dioxane gives ethylene glycol as the sole by-product. Pyruvaldehyde (methylglyoxal); 2,3-butanedione (dimethylglyoxal) and 2,3-pentanedione (ethylmethylglyoxal) can be substituted for glyoxal.

The reaction of the piperazines and glyoxal is carried out utilizing 0.5 mole to ten moles of the piperazine to each mole of glyoxal. The reaction products are the corresponding ethanone and ethanediol. If the corresponding ethanone is desired, the mole ratio of piperazine to glyoxal is preferably 0.5:1. On the other hand, to form the corresponding ethanediol, preferably two or more moles of the piperazine to each mole of glyoxal is used. If the substituted piperazine is liquid, the reaction is carried out by adding the glyoxal or alkyl substituted glyoxal in a solvent, which may be water or an alcohol. When piperazine is used, it is first dissolved in a solvent which may be water or an alcohol but preferably is an alcohol such as methanol. Other suitable solvents such as ethers or other hydrocarbons which dissolve the reactants may be used. Preferably the reaction is carried out by maintaining the piperazine either with no solvent or in a solvent such as an alcohol at a temperature between 0° C. and 150° C., more preferably between 0° and 75° C. To the liquid piperazine or substituted piperazine is added glyoxal or substituted glyoxal while maintaining good mixing which results in the reaction products of the present invention precipitating as a mixture. The reaction is illustrated by the following general equation:

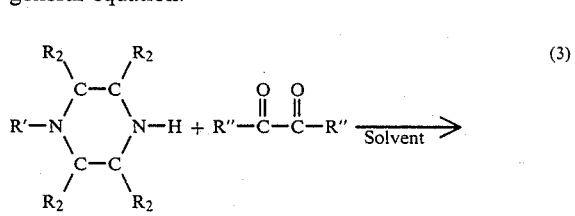

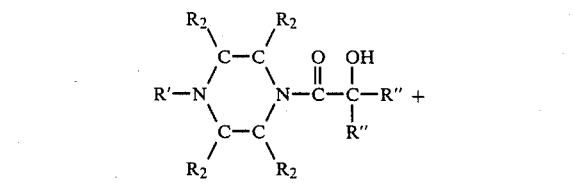

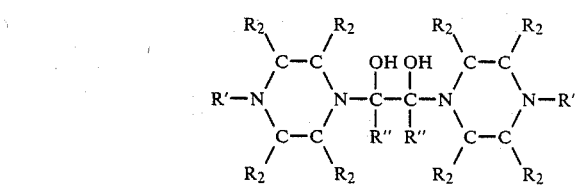

These new compositions of matter are useful as hydrochloric acid corrosion inhibitors. Further, the diol compounds may have utility as lubricant initiators, and the ethanone compounds may be used as epoxy resin hardeners, when R' is hydrogen or a hydroxy substituted alkyl.

The present invention may also be further illustrated by the following specific examples:

EXAMPLE I

To a two liter kettle equipped with a reflux condenser, addition flask, immersion thermometer, mechanical stirrer and nitrogen purge system was added 515.8 g (6 moles) piperazine dissolved in 600 ml water. The contents in the resin kettle were stirred under nitrogen at 35° C. 218 g of 40 wt % glyoxal (1.5 moles) in water were diluted further with 70 g of water and added dropwise to the reactor contents over a period of twenty minutes. The reactor contents were allowed to stir at ambient temperature for thirty minutes. The reactor mixture became yellow and cloudy. A white crystalline solid was deposited on the kettle walls. The white crystalline solid was identified as piperazine hydrate by infrared spectrometry. The reactor mixture was filtered using a sintered funnel of medium porosity by vacuum. A tan colored solid was recovered. On washing with ethanol, the tan colored solid became a white solid. Infrared spectroscopy of the white solid showed no evidence of carbonyl groups but the presence of hydroxyl groups. Electron impact and chemical ionization mass spectrometry indicated the white solid was 1,2-bis (piperazinyl) ethanediol:

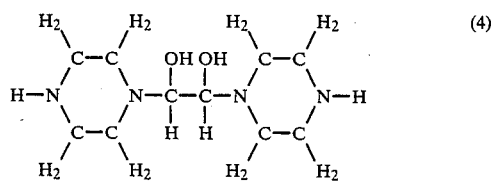

(4)

The white solid was found to contain 56.3% carbon, 8.88% hydrogen, 22.1% nitrogen and 12.72% oxygen by CHN analysis. The percent carbon, hydrogen, nitrogen and oxygen calculated from the molecular formula of 1,2-bis (piperazinyl) ethanediol is 52.2, 9.6, 24.3 and 13.9%, respectively. The percent yield for 1,2-bis (piperazinyl) ethanediol was 23.3%. The filtrate was transferred to a liter round bottom flask and water removed by rotary evaporation. A brown oily water soluble liquid remained after the rotary evaporation. Infrared spectroscopy showed the brown oil liquid consisted of piperazine hydrate, a compound containing an amide group (1645 cm$^{-1}$) and 1,2-bis(piperazinyl)ethanediol. Electron impact ionization mass spectroscopy indicated the compound containing the amide group was 2-hydroxy-1-(1-piperazinyl) ethanone:

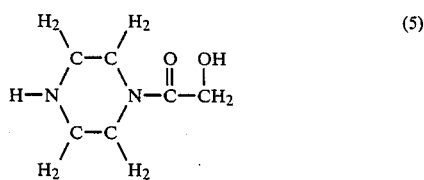

(5)

EXAMPLE II

To a two liter kettle equipped with a reflux condenser, addition flask, immersion thermometer, mechanical stirrer and nitrogen purge system was added 257.6 g (3.0 moles) piperazine dissolved in 1300 ml methanol. The apparatus was cooled with an ice bath to 0° to 5°·C. 216.6 g of 40 wt % glyoxal (1.5 moles) in water was added dropwise to the reactor contents over a period of forty-three minutes. The reactor contents were a yellow milky color. A white solid was recovered from the reactor mixture by filtration using a 600 ml pyrex sintered funnel of the medium porosity by vacuum. The white solid was washed with benzene, ethanol and benzene and dried under vacuum at 100° C. Electron impact and chemical ionization mass spectrometry indicated the white solid was 1,2-bis (piperazinyl)ethanediol. The white solid was gound to contain 54.7% carbon, 22.8% nitrogen, 9.09% hydrogen, 13.21% oxygen, 10.6% tertiary nitrogen and 11.7% secondary nitrogen. The percent carbon, nitrogen, hydrogen, oxygen, tertiary nitrogen and secondary nitrogen calculated from the molecular formula of 1,2-bis (piperazinyl)ethanediol is 52.2, 24.3, 9.6, 13.9, 12.1 and 12.1%, respectively. Bis(1,2-piperazinyl) ethanediol was observed to melt between 190°–208° C. The melted bis(1,2-piperazinyl)ethanediol was a reddish brown liquid. The percent yield for bis(1,2-piperazinyl) ethanediol was 31.97%.

The foregoing example illustrates a preferred process for the preparation of the compounds of the inventive process. The use of the alcohol eliminates the piperazine hydrate, which is formed when water is used as the solvent, and thus makes the separation of the compounds easier.

The utility of the compositions produced by the process of the present invention are illustrated by the following example:

EXAMPLE III 1,2-bis(piperazinyl)ethanediol and an aqueous solution containing 1,2-bis(piperazinyl)ethanediol, 2-hydroxy-1-(1-piperazinyl)ethanone and piperazine hydrate were evaluated as corrosion inhibitors in acid and gas conditioning applications.

In the acid corrosion inhibition study, a test tube containing 0.2% of the inhibitor, a carbon steel coupon and 10% hydrochloric acid were heated in a one liter Parr bomb for 6 hours at 80° C. 1,2-bis(piperazinyl)ethanediol and the aqueous solution containing 1,2-bis(piperazinyl)ethanediol, 2-hydroxyl-1-(1-piperazinyl)ethanone and piperazine hydrate exhibited 67% and 55% corrosion inhibition, respectively.

In the gas conditioning corrosion inhibition study, a test tube containing 0.2% of the inhibitor, a mild steel coupon and 25 milliliters of 30% aqueous monethanolamine saturated with carbon dioxide was heated in a 1 liter Parr bomb at 140° C. for 20.5 hours. 1,2-Bis(piperazinyl)ethanediol and the aqueous solution containing the products from the reaction of piperazine and glyoxal exhibited 26% and 25% corrosion inhibition, respectively.

While the invention has been described herein with reference to certain specific materials, procedures and examples, it is understood that the invention is not restricted to the particular materials, combination of materials and procedures selected for the purpose of illustration. Numerous variations of such details can be employed by those skilled in the art within the scope of this invention which is defined by the appended claims.

I claim:

1. A process for preparing 1,2-bis (piperazinyl) ethanediol and 2-hydroxy-1-(1-piperazinyl) ethanone or derivative products thereof wherein alkyl, non-heterocyclic aryl, or non-heterocyclic aralkyl groups are substituted for one of the hydrogen moieties on each carbon atom which comprises:

reacting from 0.5 to 10 moles of:

$$\begin{array}{c} R_2 \quad R_2 \\ \diagdown \quad \diagup \\ H-C-C-H \\ \diagup \qquad \diagdown \\ R'-N \qquad N-H \\ \diagdown \qquad \diagup \\ H-C-C-H \\ \diagup \quad \diagdown \\ R_2 \qquad R_2 \end{array} \quad (A)$$

where R is hydrogen; $C_1$ of $C_{10}$ alkyl; non-heterocyclic aryl or non-heterocyclic aralkyl; and R' is hydrogen or $C_1$ to $C_{20}$ alkyl; either with no solvent or in a solvent, but without sodium carbonate or bicarbonate, with 1.0 mole of:

$$\begin{array}{c} O \quad O \\ \| \quad \| \\ R''-C-C-R'' \end{array} \quad (B)$$

where R'' is hydrogen or $C_1$ of $C_4$ alkyl to produce 1,2-bis(piperazinyl) ethanediol or 2-hydroxy-1-(1-piperazinyl) ethanone or derivative products thereof where alkyl, nonheterocyclic aryl, or nonheterocyclic aralkyl groups are substituted for the hydrogen moieties.

2. The process of claim 1 wherein the reaction is carried out in a solvent at a temperature in the range of about 0° to 150° C.

3. The process of claim 1 wherein after the reaction takes place, 1,2-bis(piperazinyl) ethanediol and 2-hydroxyl-1-(1-piperazinyl) ethanone or the corresponding substituted product thereof is recovered.

4. The process of claim 2 wherein the solvent for components (A) and (B) is water, alcohol, or ether.

5. The process of claim 4 wherein the solvent for component (A) is methanol and the solvent for component (B) is water.

6. The process of claim 4 where the solvent for component (A) is methanol and the solvent for component (B) is methanol.

7. The process of claim 1 wherein the reaction is carried out at a temperature in the range of from about 0° to 75° C.

8. The process of claim 3 wherein the recovery step is carried out by filtration followed by solvent extraction.

9. The process of claim 8 wherein solvent extraction involves using ethanol and benzene as the solvents.

10. The process of claim 3 wherein the recovery step is carried out by distillation.

11. The process of claim 1 wherein component (B) is added to component (A) while the reaction mixture is being vigorously stirred.

* * * * *

UNITED STATES PATENT AND TRADEMARK OFFICE
CERTIFICATE OF CORRECTION

PATENT NO. : 4,837,324

DATED : June 6, 1989

INVENTOR(S) : Duane S. Treybig

It is certified that error appears in the above-identified patent and that said Letters Patent is hereby corrected as shown below:

On the front page, under Other Publications, "Cycle Urea-Glyoxal" should read -- Cyclic Urea-Glyoxal -- .

On the front page, under Other Publications, "Imidazolidin-1414yl" should read -- Imidazolidin-1-yl -- .

Column 2, line 6, "1-dodecyll" should read -- 1-dodecyl-1 -- .

Column 2, line 7, "puperazine" should read -- piperazine -- .

Column 4, line 18, "gound" should read -- found -- .

Column 5, line 20, "of" should read -- to -- .

Column 5, line 29, "of" should read -- to -- .

Signed and Sealed this

Sixteenth Day of October, 1990

Attest:

HARRY F. MANBECK, JR.

*Attesting Officer*      *Commissioner of Patents and Trademarks*